United States Patent
Grewe et al.

(10) Patent No.: US 10,028,820 B2
(45) Date of Patent: Jul. 24, 2018

(54) CAROTID ARTERY BLOOD FILTER PLUGGING ALARM

(71) Applicant: Cook Medical Technologies LLC, Bloomington, IN (US)

(72) Inventors: David D. Grewe, Grand Junction, MI (US); Santanu Chandra, W. Lafayette, IN (US)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 212 days.

(21) Appl. No.: 15/075,347

(22) Filed: Mar. 21, 2016

(65) Prior Publication Data
US 2016/0302907 A1 Oct. 20, 2016

Related U.S. Application Data

(60) Provisional application No. 62/147,242, filed on Apr. 14, 2015.

(51) Int. Cl.
*A61F 2/01* (2006.01)

(52) U.S. Cl.
CPC .......... *A61F 2/01* (2013.01); *A61F 2002/016* (2013.01); *A61F 2210/009* (2013.01); *A61F 2230/0006* (2013.01); *A61F 2250/0067* (2013.01)

(58) Field of Classification Search
CPC .................. A61F 2/01; A61F 2002/016; A61F 2210/009; A61F 2230/0006; A61F 2250/0067; A61F 2002/011; A61F 2/013; A61F 2002/018; A61B 17/221; A61B 2017/2212
See application file for complete search history.

(56) References Cited

U.S. PATENT DOCUMENTS

| | | | |
|---|---|---|---|
| 3,330,269 | A | 7/1967 | Pieper |
| 3,734,083 | A | 5/1973 | Kolin |
| 4,507,976 | A | 4/1985 | Banko |
| 5,002,090 | A | 3/1991 | Ichikawa et al. |
| 5,188,728 | A | 2/1993 | Traonvoez et al. |
| 5,462,525 | A | 10/1995 | Srisathapat et al. |
| 6,181,128 | B1 | 1/2001 | Schroeder |
| 6,770,070 | B1 | 8/2004 | Balbierz |

(Continued)

FOREIGN PATENT DOCUMENTS

| WO | WO 2005/072169 A2 | 8/2005 |
|---|---|---|
| WO | WO 2005/107639 A2 | 11/2005 |
| WO | WO 2014/016359 A1 | 1/2014 |

OTHER PUBLICATIONS

Extended European Search Report dated Sep. 1, 2016.

*Primary Examiner* — Katrina Stransky
(74) *Attorney, Agent, or Firm* — Brinks Gilson & Lione

(57) ABSTRACT

An intravascular filter device having a flexible arm which comprises a portion of an alarm system for detecting filling or plugging of the filter by captured emboli is described. The flexible arm may be made of ferromagnetic material, a magnet, or have at its tip a magnet which, as it moves under systolic and diastolic pressures, generates a signal detectable by an electrical sensor or a magnetometer. The signals from each of a pair of artery filters may be measured and compared to determine whether one filter is plugged. A system for detection and a method of use are also provided.

20 Claims, 4 Drawing Sheets

(56) References Cited

U.S. PATENT DOCUMENTS

| | | |
|---|---|---|
| 7,584,657 B2 | 9/2009 | Heller et al. |
| 7,963,989 B2 | 6/2011 | McEwan |
| 2003/0125790 A1 | 7/2003 | Fastovsky et al. |
| 2003/0153943 A1 | 8/2003 | Michael et al. |
| 2004/0044393 A1 | 3/2004 | Yarden et al. |
| 2005/0055078 A1* | 3/2005 | Campbell ............... A61F 2/90 623/1.11 |
| 2007/0093744 A1* | 4/2007 | Elmaleh ........... A61B 17/22004 604/22 |
| 2008/0208245 A1 | 8/2008 | Hoffman |
| 2009/0248060 A1 | 10/2009 | Schneider et al. |
| 2013/0184742 A1* | 7/2013 | Ganesan ................. A61F 2/01 606/200 |
| 2014/0081154 A1 | 3/2014 | Toth |
| 2014/0135815 A1* | 5/2014 | Hyde ................ A61B 5/02007 606/200 |
| 2014/0243880 A1 | 8/2014 | Schotzko et al. |

* cited by examiner

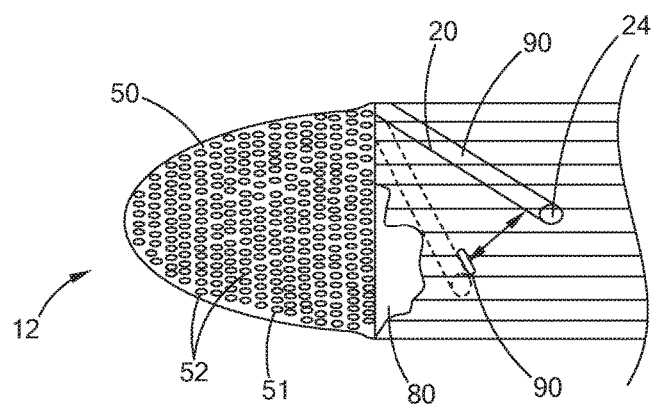
FIG. 5
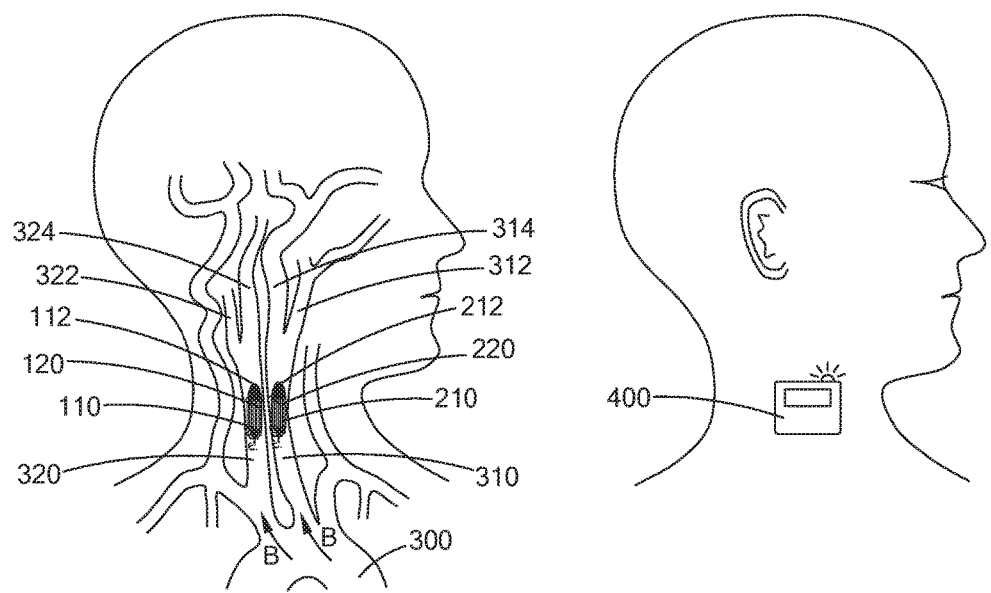
FIG. 6
FIG. 7

CAROTID ARTERY BLOOD FILTER PLUGGING ALARM

CROSS-REFERENCE TO RELATED APPLICATIONS

This application claims the benefit of priority under 35 U.S.C. § 119(a) to U.S. Provisional Application No. 62/147,242, filed Apr. 14, 2015 all of which are hereby incorporated by reference in their entirety.

BACKGROUND

The present invention relates to medical devices. More particularly, the invention relates to an intravascular filter which has a distal filter basket which allows blood to flow through, but captures emboli, the filter device having a flexible arm having magnetic characteristics and which serves as a component of an alarm which allows a physician to know whether the filter has become filled or clogged by emboli or other debris.

Filtering devices are percutaneously placed in body vessels of a variety of medical patients, including but not limited to trauma patients, orthopedic surgery patients, neurosurgery patients, or in patients having medical conditions requiring bed rest or non-movement. During such medical conditions, the need for filtering devices arises due to the likelihood of thrombosis in the peripheral vasculature of patients wherein thrombi break away from the vessel wall, risking downstream embolism or embolization. For example, patients in danger of suffering strokes may have a filter placed in each of the left and the right carotid arteries, potentially in the common portion of the carotid arteries, as many strokes are caused by emboli originating from the carotid bifurcation.

Typically, the filtering devices are permanent implants, each of which remains implanted in the patient for life. However, it can be desirable to remove or empty implants when they fill. In the case of a carotid artery filter, a clogged or filled filter can result in reduced blood flow to the brain. Because filters can fill gradually, it is advantageous to have a way of monitoring the status of each filter regularly and noninvasively. However, large thromboemboli can also break off and cause rapid filling of the filter as well.

Implanted medical devices which incorporate an element which can generate a signal that can be detected by a device which is outside of the body, or that can modulate a signal that is originates outside the body. The detector may be small and portable, and which produces minimal or no radiation will be helpful in better monitoring the status of a patient's condition.

It is desirable to include a built-in way of monitoring blood flow through a filter, which correlates to the amount of embolic material trapped in the filter, so that timely intervention can be made in a patient in need thereof.

SUMMARY

According to a first aspect of the present invention, an intravascular device for capturing emboli is provided. The intravascular device includes a device body having a longitudinal axis. The device body comprises a filter basket comprising a filter portion and a lip attached to the filter portion, the lip defining an opening to the filter portion, the filter portion extending distally to a filter end from the lip and having apertures formed therethrough for blood flow. The device body also comprises a plurality of elongate members each having a proximal end and a distal end. The distal ends are attached to and disposed circumferentially on the lip of the filter basket, each elongate member extending proximally to its proximal end, the elongate members defining a device interior therebetween. The device further includes a flexible arm comprising a first end attached to the device body and extending into the device interior to a second end, a magnetic element being disposed at the second end of the flexible arm such that movement of the flexible arm is indicative of capture of emboli within the filter portion.

In another embodiment, a system for monitoring the filling of a filter with emboli is provided. Included in the system is an intravascular device includes a device body having a longitudinal axis. The device body comprises a filter basket comprising a filter portion and a lip attached to the filter portion, the lip defining an opening to the filter portion, the filter portion extending distally to a filter end from the lip and having apertures formed therethrough for blood flow. The device body also comprises a plurality of elongate members each having a proximal end and a distal end. The distal ends are attached to and disposed circumferentially on the lip of the filter basket, each elongate member extending proximally to its proximal end, the elongate members defining a device interior therebetween. The device further includes a flexible arm comprising a first end attached to the device body and extending into the device interior to a second end, a magnetic element being disposed at the second end of the flexible arm such that movement of the flexible arm is indicative of capture of emboli within the filter portion. The system further includes an external detector for detecting the signal generated by the flexible arm, the signal comprising at least one of a voltage, a current, and an electromagnetic field. Such a detector may comprise a magnetometer.

According to another aspect of the present invention, there is provided a method for detecting embolic fragments in an intravascular device. The method comprises steps including implanting an intravascular device into the blood vessel, the device comprising a filter basket, the device having a flexible arm therewithin comprising a magnetic element disposed thereon such that movement of the flexible arm is indicative of blood flow through the filter basket defining a baseline signal; generating an experimental signal; and comparing the experimental signal to the baseline signal to determine the presence of captured emboli within the intravascular device.

Further aspects, features, and advantages of the invention will become apparent from consideration of the following description and the appended claims when taken in connection with the accompanying drawings.

BRIEF DESCRIPTION OF THE DRAWINGS

Preferred embodiments of the present invention are described below, by way of example only with reference to the accompanying drawings in which:

FIG. 5 a close-up view of the distal end of an intravascular filter device in which the filter has captured sufficient emboli to interfere with the movement of the flexible arm;

FIG. 6 is a view of two intravascular filter devices implanted in the carotid arteries of a patient in accordance with another embodiment of the present invention; and FIG. 7 is a view of a detector being used to monitor the status of a carotid artery filter in accordance with another embodiment of the present invention.

DETAILED DESCRIPTION

It is to be understood that the figures are schematic and do not show the various components to their actual scale. In many instances, the figures show scaled up components to assist the reader.

In this description, when referring to a deployment assembly or a medical device, the term distal is used to refer to an end of a component which in use is furthest from the surgeon during the medical procedure, including within a patient. The term proximal is used to refer to an end of a component closest to the surgeon and in practice in or adjacent an external manipulation part of the deployment or treatment apparatus.

"Substantially" or derivatives thereof as used herein will be understood to mean significantly or in large part. The terms "substantially" or "about" used herein with reference to a quantity includes variations in the recited quantity that are equivalent to the quantity recited, such as an amount that is equivalent to the quantity recited for an intended purpose or function.

A component which is "angled away" from another component or space may or may not share a vertex with the component from which it is angled away. The angle formed when a component is "angled away" from another component is a non-zero angle; that is, the component which is angled away does not run parallel to, or entirely overlie, the component from which it is angled away.

As used herein, a "magnetic element" is any substance or element which is capable of creating, responding to, or modifying a magnetic or electromagnetic field. For instance, a magnetic element may be a magnet itself, or it may be a ferromagnetic material or component. Magnetic elements include but are not limited to those incorporating a transition metal such as iron, cobalt, and nickel; a metalloid such as boron, carbon, silicon, phosphorous, and aluminum; a rare earth metal; an alloy; or any other component which attracts, repels, is attracted by, or is repelled by a magnet.

The use of an intravascular filter bearing a signal-generating mechanism which can work in concert with a sensor outside of the body to create an alarm when the filter becomes partially plugged when it captures emboli can be of benefit in preventing embolic stroke. A great variety of patients are envisioned to be candidates for installation and use of such filters, particularly those who have suffered stroke in the past or are determined to be pre-stroke. Patients who may be considered susceptible to stroke include those suffering atrial arrhythmia. Other patients who could be aided by such a device would be those undergoing cardiac bypass or heart valve replacement procedures. In these procedures, patients might be administered medications with undesirable side effects to minimize the chances of embolus generation and stroke. One benefit of a device in accordance with the principles of this invention would be to minimize the need for such medications.

Figure 1:
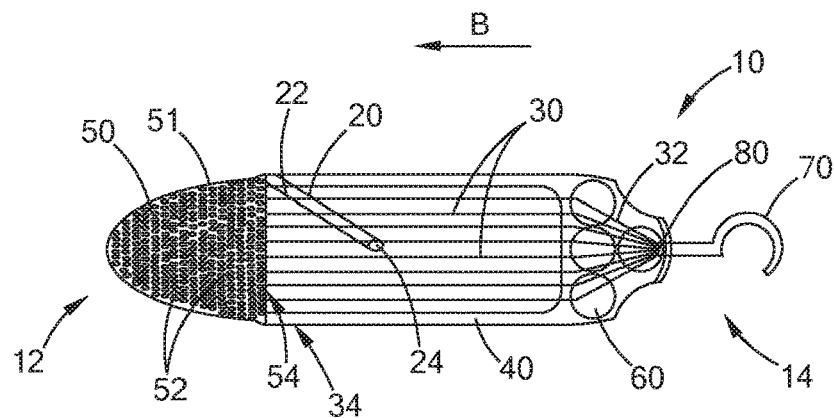
FIG. 1 is a side view of an intravascular filter in accordance with one embodiment of the present invention in a first configuration during a period of diastolic blood flow.

FIG. 1 depicts an intravascular filter device 10 in accordance with the principles of the present invention. The device 10 extends from distal end 12 to proximal end 14 and has a device body comprising basket 50 and elongate members 30. The device 10 has a collapsed, or undeployed, state, in which the device has a relatively small diameter and profile and in which it can be placed within a delivery apparatus for percutaneous delivery of the device to the target vessel, and an expanded, or deployed, state, in which the diameter and profile of the device expand from the relatively small dimensions to a size which would allow the device to fit securely along the walls of the vessel where the filter is to be installed, such as a common carotid artery.

The basket 50 comprises a lip 54 which extends around its proximal end and extends distally to the distal end 12 of the device body and a filter portion 51 which extends distally from the lip. In the deployed state, the lip takes on a substantially circular shape and has a radius extending from the longitudinal axis to the lip, and a circumference. In one embodiment, the lip 54 may be a separate component, such as a unitarily formed ring comprising a shape memory metal. In another embodiment, the lip 54 is simply the edge of the filter portion 51 of the device. The filter portion 51 is a porous structure which allows the flow of blood therethrough, but the pores 52 are not so large as to allow emboli to pass through. The filter portion may comprise a mesh or foil made of a shape memory metal, such as a nickel-titanium alloy, particularly NITINOL. If made of such a metal, the pores may be laser-cut into a generally basket-shaped metal body, or the basket may be woven of shape memory metal wires. The filter portion may also or alternatively comprise fibers of biocompatible polymer and may be woven. Overall, the basket 50 or the filter portion may take on any shape in the deployed state, such as a semi-spheroid, a cup shape, a cylinder, a substantially conical shape, a portion of an ellipse, or any other shape.

The plurality of elongate members 30 are attached to or emanate from the lip 54 of basket 50. In one embodiment, the elongate members are arranged circumferentially about the lip 54, spaced substantially evenly thereabout. The distal ends 34 of each elongate member 30 are attached to lip 54 and the elongate members extend substantially proximally to their proximal ends 32. In one embodiment, such as that illustrated in FIG. 1, the elongate members 30 run substantially parallel to the longitudinal axis for a first distal portion of their lengths and the angle inward toward the longitudinal axis or the center of the device such that their proximal ends 32 converge at a device hub 38. The elongate members may be made of a polymer, such as DACRON, or a shape memory material, such as a nickel-titanium alloy. Any material or configuration which permits the device to be collapsible into an undeployed state and, upon delivery to the target vessel, expand into the deployed configuration, is acceptable. A shape memory metal such as a nickel-titanium alloy can be particularly favorable for this as such metals can undergo a transition from room temperature to return to an expanded, remembered state at body temperature, which may improve patency with the vessel wall.

Further, the elongate members 30 can be coated with flexible, tough coating of polyethylene glycol diacrylate (PEGDA). PEGDA is a biocompatible polymer that can be effective in preventing coagulation. Can include a nitric oxide-releasing chemical. Alternatively or additionally, the elongate members 30 may comprise a polyurethane/polyethylene glycol with a diazeniumdiolate nitric oxide donor in the coating. Such a composition may be competent to release nitric oxide over the course of about two months. If endothelialization of the device is desired while adhesion of platelets is discouraged, nitric oxide release can be coupled with incorporation of the cell adhesive peptide sequence tyrosine-isoleucine-glycine-serine-arginine (YIGSR) derived from laminin into the coating.

Continuing with the description of FIG. 1, a flexible arm 20 is also provided. The arm 20 has a first end and extends to a second end. Such an arm 20 may be attached to a portion of the device body or may be formed integrally with it when the device is initially made. The first end of flexible arm 20 can be attached to or extend from the lip 54 of the basket 50, or to elongate members 30. The arm may be made of any flexible material which is capable of moving during systole and diastole to produce a discernible signal. In one embodiment the arm is made of a flexible material such as a nickel-titanium alloy. In another embodiment, the arm is a hinged, rigid arm made of a rigid material, and hence is flexible due to flexing at the hinge during systole and diastole.

At the second end of flexible arm 20 is magnet 24. The magnet is small and relatively strong. The magnet 24 may comprise neodymium or may be made of another magnetic material. The remainder of the device should not be attractive nor repulsive to the magnet. The magnet 24 is small enough that it permits movement of the flexible arm with blood flow rates resulting from systolic and diastolic pressures.

A sleeve 40 may optionally overlie and surround a portion of the device body, particularly the elongate members 30. In the embodiment illustrated in FIG. 1, the sleeve 40 surrounds the entire lengths of the elongate members 30 and contains holes 60, which serve as a first, porous filter. Such a proximal filter element prevents dislodged emboli which would plug the finer filter basket 50 entirely to avoid complete blockage of the vessel. The sleeve 40 may be made of any acceptable biocompatible polymer which allows for collapse into a delivery catheter and deployment of the intravascular filtration device 10.

Optionally, if the filter is to be retrieved, a retrieval hook 70 may be provided at proximal end 14. When a practitioner sees fit to remove the filter from the artery of the patient, any suitable retrieval device may engage hook 70 and extract the filter.

The flexible arm 20 moves in response to the changing flow of blood through the filter in response to the pressure cycle of the vasculature. The arm 20 rests proximally during diastole and moves distally under systole. In a patient having no emboli lodged in the filter, the degree of motion between two installed filters would be relatively similar. However, in a patient whose endogenous blood pressure feedback system is operating correctly, the arteries would vasoconstrict in order that the needed supply of blood oxygen would pass through the artery that contains the partially plugged filter. The contralateral carotid artery blood flow rate would then exceed the other carotid artery's blood flow rate because its filter would not be plugged or filled with emboli. Alternatively, the mechanism of action may differ in different patients having non-identical conditions and is not intended to be limiting.

Continuing in the description of FIG. 1, the filter is shown under diastolic conditions, when the aortic pressure is relatively low. The direction of blood flow is noted with arrow B. During diastole, the magnet 24 is as far in the proximal direction as it will be during deployment. The arm 20 is shown extending to its proximal extreme in FIG. 1.

Figure 2:
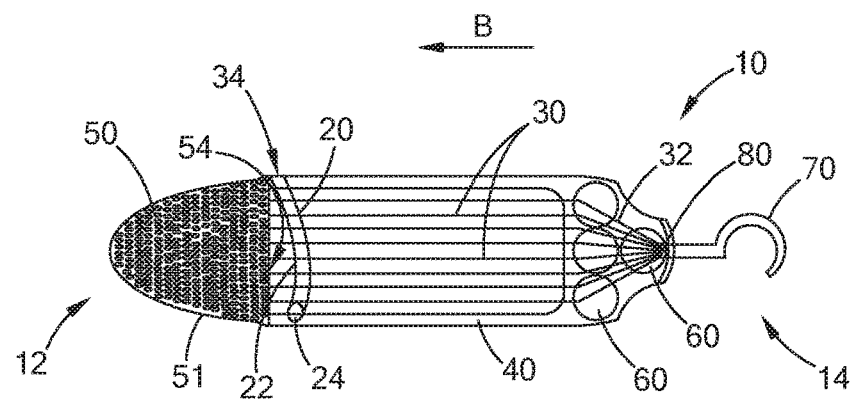
FIG. 2 is a side view of the intravascular filter of FIG. 1 in a second configuration during a period of systolic blood flow.

FIG. 2, in contrast, shows an empty filter device 10 during systole. The forces in the carotid artery due to the flow of blood have forced the arm distally, with the magnet 24 arcing through the lumen of the vessel and of the device body toward the distal end 12. A sensor placed outside of the body which generates an electromagnetic field would respond with a signal of the highest magnitude to the most extreme movement of the magnet 24 to the distal end.

Figure 3:
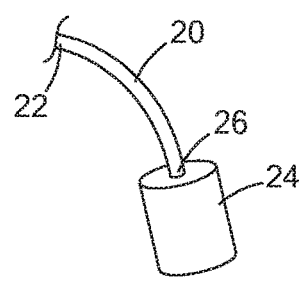
FIG. 3 is a close-up view of flexible arm and magnetic element in accordance with one embodiment of the present invention.

FIG. 3 shows a close-up view of a flexible arm. The magnet 24 has been heat set onto arm 20 at junction point 26. The magnet 24 may also be attached to the flexible arm 20 by any other means which does not interfere with its magnetic characteristics.

Because dislodging and capture of an embolus is a relatively stochastic event, it is likely that only one of two implanted carotid arteries will capture an embolic fragment and become plugged at one time. Hence, measures of relative flow in the two filters are likely to be a useful measure of filter plugging and embolus capture. To improve reliability of relative signals produced by the pair of filters, it will be advantageous to subject the patient to similar ambient conditions at each reading.

In an alternative embodiment, the flexible arm may not have a magnet attached to its second end. Rather, the arm in this embodiment will itself be made of ferromagnetic material. Movement of the ferromagnetic arm itself will cause a modulation of the magnetic field that can be detected. The electronic unit used to detect signal would have the capability of indicating an absolute change in blood flow velocity through the filter and the values obtained would be able to indicate any difference in flow between the two filters, which would correlate to the degree to which each filter is plugged. In such an embodiment, the arm itself would not necessarily have to be flexible, but instead could be flexibly attached to the device body either at one of the elongate members of the frame or at the lip of the filter basket and move unitarily with systolic and diastolic pressures.

Although intravascular devices of this construction are proposed to be used in the carotid arteries, other areas in the body may also benefit from a filter bearing an alarm. For example, two filters could be implanted into each of the renal arteries to prevent debris from entering kidney and could provide similar readouts when they became plugged.

Figure 4A:
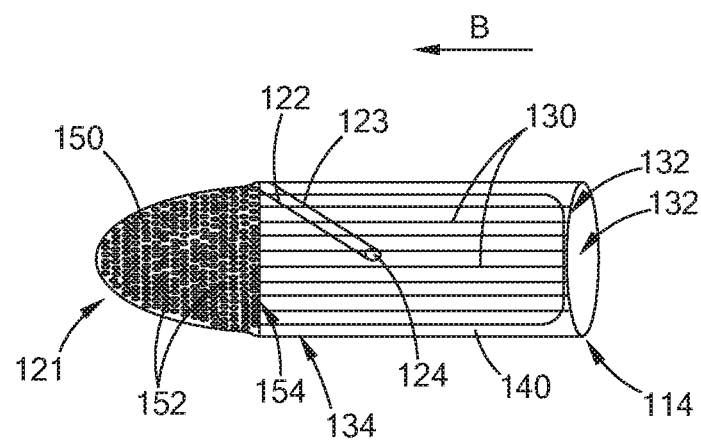
FIG. 4A is a side view of an intravascular filter in accordance with another embodiment of the present invention.

Turning now to FIG. 4A, another embodiment of a filter in accordance with the principles of the device is illustrated. In this embodiment, the proximal end 114 of the device is an open end defined by the circumferential arrangement of proximal ends 132 of elongate members 130. Such an arrangement gives an overall cylindrical shape to the proximal end of the device body. The open end is as wide as the vessel itself and remains patent against the internal wall of the vessel into which it has been deployed. Hence no emboli will escape between the filter and the blood vessel wall. This allows for the flow of all materials, including emboli, which enter the bloodstream through the mouth of the device for eventual capture in or passage through the distal basket 150.

Figure 4B:
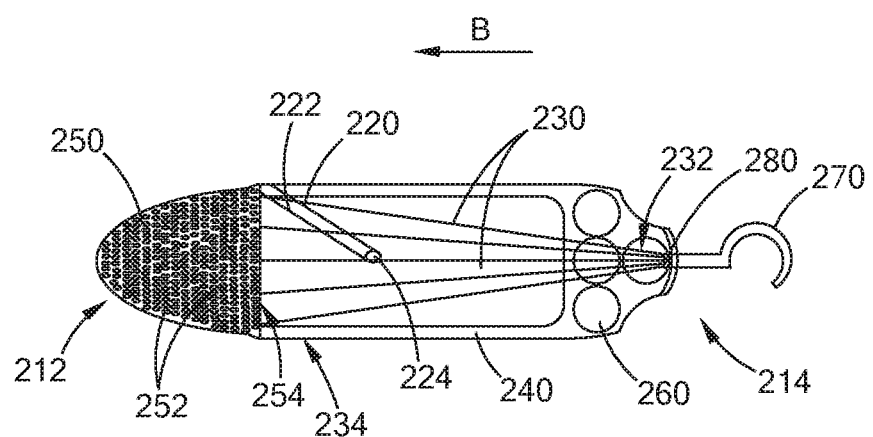
FIG. 4B is a side view of an intravascular filter in accordance with another embodiment of the present invention.

FIG. 4B. illustrates another embodiment of an intravascular device in accordance with the principles of the present invention. In this embodiment, the elongate members 230 are attached to the lip 254 of the basket 250, but rather than running parallel to the longitudinal axis, the elongate members 230 are of a single segment and converge at hub 280 to form a substantially conical structure inside of sleeve 240. The sleeve 240 gives the device body its ability to remain patent against the inner wall of the artery in which it is deployed.

Figure 4C:
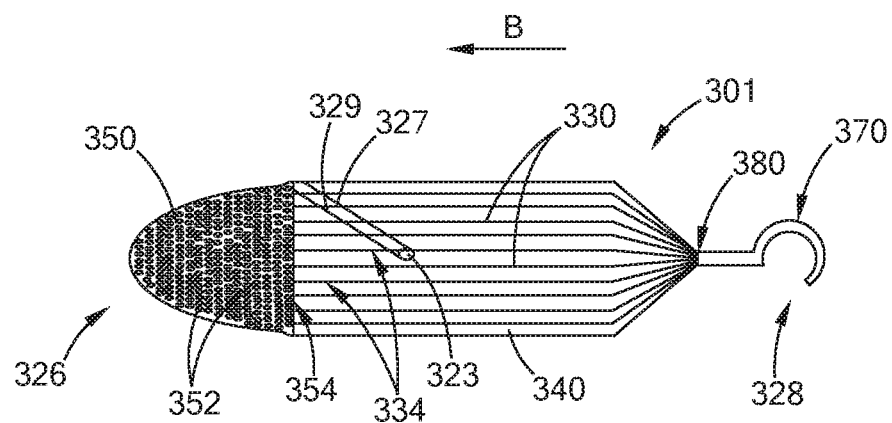
FIG. 4C is a side view of an intravascular filter without an outer sleeve or sheath in accordance with another embodiment of the present invention.

FIG. 4C illustrates a further embodiment which lacks an outer sleeve. In this arrangement, the elongate members 330 are in direct contact with the inner wall of the artery, at least along a relatively distal portion of their lengths. The elongate members 330 might converge, for instance, at a hub 380. In such an embodiment it may be advantageous to form the struts of a shape memory metal.

Figure 4D:
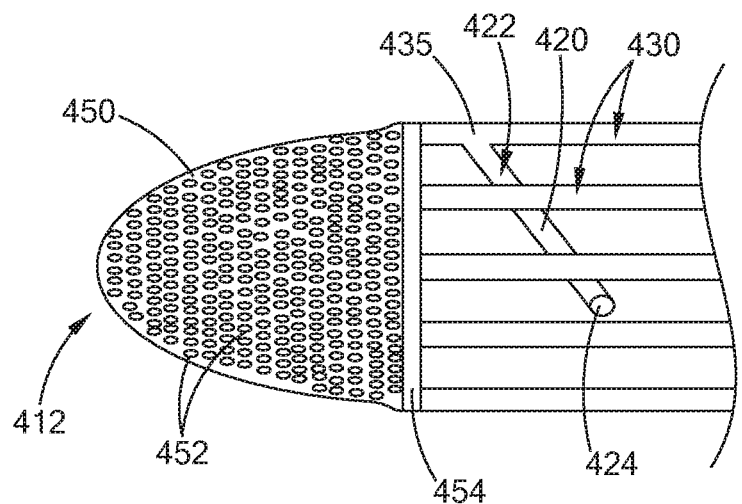
FIG. 4D is a close-up view of the distal end of an intravascular filter device in accordance with another embodiment of the present invention.

FIG. 4D is a close-up view of the distal end of a device in accordance with another embodiment of the invention. Whereas all previous illustrations have shown the flexible arm attached at its first end to the lip of the basket portion, FIG. 4D shows the first end 422 of flexible arm 420 extending from an elongate member 430 at junction 435. In the illustrated embodiment, the flexible arm 420 is formed integrally with the device body, but in another embodiment it may be formed separately and attached by any well-known means after manufacture. Additionally, flexible arm 420 may be configured in its resting position to point in a direction normal the longitudinal axis or even distally, rather than proximally as depicted.

Advantages of intravascular filtration devices of any of the preceding designs are numerous. In one aspect, the porosity of the filter basket allows for installation of the device without diversion or interruption of blood flow. The collapsed device is simply placed in the lumen of the artery into which it is to be deployed, expanded to its full diameter, and blood continues to flow along its natural path throughout the procedure. Second, observation of the condition of the filters is based on a predictable, dynamic flow, and the signal can be generated by a small, portable sensor, obviating the need for larger, more expensive, and more complex machinery associated with imaging technologies such as X-ray and magnetic resonance imaging. Moreover, because the flexible arm generates a detectable signal which does not rely upon visual determination or comparison to a reference wire, there is no confounding variable of human interpretation of, for instance, the relative difference between positional spacings of a reference and an experimental wire, or assigning meaning to small and potentially unpredictable curving of a wire element which must be visually ascertained. Finally, the motion of the flexible arm produces a signal numerous times per minute at predictable periods. Such repetition permits collection of multiple data points over the course of a short period of time in a single observation period.

FIG. 5 illustrates the consequence of emboli 80 partially filling a filter device 10. As shown, the embolus 80 has been captured in basket 50 and the flexible arm 20 starts at diastolic position 90 and is only capable of moving to position 92 during systole. The flexible arm 20 may have limited motion due to physical collision with the embolus 80, or due to a limited flow pressure differential due to plugging of the filter, or both. This represents a limited range of motion compared to an empty filter 10, and in turn because magnet 24 is not moving as far through the field generated by the sensor, the signal it generates for detection is attenuated. This alerts the physician that there may be emboli present. This non-limiting example presents a single scenario in which such a filter alarm will be useful. In another example, the filter portion of the basket may not be filled to such an extent that physical movement of the flexible arm is impeded, but the presence of emboli in the device changes the blood flow pattern through the vessel and through the device such that the magnitude of the movements of the flexible arm are altered.

FIG. 6 depicts a view of a patient who has a filter device implanted in both carotid arteries. Right device 110 is deployed in right common carotid artery 320, and left device 210 is deployed in left common carotid artery 310. Emboli which might travel in the direction of blood flow B through the aortic arch 300 and into the carotid arteries 310/320 should be trapped toward the distal ends 112/212 of the devices 110/210 prior to reaching the external carotid arteries 312/322 or internal carotid arteries 314/324 and traveling toward the brain and resulting in embolic stroke. Measurements taken from the movement of flexible arms 120/220 will inform a practitioner as to whether emboli are trapped in the filter baskets.

FIG. 7 shows one means of detection of the signal generated by an intravascular filter in accordance with the principles of the present invention. A detector 400 is held to the neck of a patient who bears two intravascular filters and a readout is taken as the flexible arm causes the magnets of the devices to move with systolic and diastolic pressures.

Many different types of detectors or sensors in a system that can operate under the principles of the present invention can be envisioned. In one aspect, the sensor can make use of the Hall effect, in which the motion of the magnet produces a measurable voltage. The sensor or detector 400 could be constructed such that it has an element through which a current is passed. When the sensor or detector is held in the magnetic field of the magnet 24 at the end of flexible arm 20, a charge separation occurs in the sensor according to the magnitude of the magnetic field. This so-called Hall voltage can then be interpreted as a degree of fullness of the filter basket with thromboemboli.

In one aspect, the detector may include a coil connected to an ammeter which will detect an electrical current induced in the coil by the motion of the magnet nearby. An alternating current may be detected. In another aspect, a voltage may instead be detected. Alternatively, a sensor may contain a microelectromechanical (MEMS) device for detecting and measuring the magnetic field generated by the magnet of an intravascular filter. When the flexible arm moves in response to the natural cycle of systole and diastole, it will generate a voltage as it moves through an electromagnetic field generated by the sensor.

To ensure more certain interpretation of signals generated by the moving magnets, the sensor must be calibrated to discern the tendencies of a particular patient. In a calibration protocol, a baseline signal is measured shortly after installation. When monitoring, a comparison of the signal generated will be proportionate to the flow rate through the filter, which is proportionate to the degree to which a filter is plugged or full of emboli. Comparing the signal generated from one filter to the baseline signal is one way of detecting possible filling of the filter with emboli. Comparing the experimental signal generated by one filter to the experimental signal generated by the other filter is another way of detecting plugging with emboli.

The detector may be capable of reporting the device on a display or through a sound-making mechanism, such as a beeper or a speaker, on its body. Alternatively or additionally, the detector may contain a wireless transmitter which can transmit a signal to a remote receiver. A receiver can include, for example, a cell phone or a smart watch, which may optionally have additional applications installed which are configured to communicate with the detector.

Because blood pressure is known to fluctuate throughout the day, it may be useful to take multiple measurements in a single day. For instance, the absolute magnitude of signal may be lower just after waking from overnight sleep and may be higher several hours later. However, the signal generated by both filters should increase and decrease proportionately in the absence of filling or plugging.

In order to provide precise measurements after implantation and through several subsequent readings, it may be advantageous to temporarily install a cradle or a similar holding device on the neck of the patient. Such a cradle would hold the detector 400 in a fixed, repeatable location corresponding to the location of the filters. This would permit the amount of signal to be maximized when reported and would provide an initial substantiation that the filters are working as intended shortly after installation. As an alternative to using a single detector, it may also be beneficial to use two detectors which might optionally be kept in place in their own dedicated cradles.

When a plugged filter is detected a number of options are possible. First, a physician could intervene and use suction to aspirate the emboli out of the filter. Alternatively, the practitioner could use a retrieval device to capture the plugged filter and the emboli trapped therein. The doctor could additionally or alternatively administer a drug or drugs to reduce the quantity of circulating thromboemboli and inhibit their formation. An intervention could also include placement of a new carotid artery filter at the site from which the plugged filter was removed. Drugs which may be administered during the intervention to assist in destroying thrombi and emboli include tissue plasminogen activators such as alteplase, reteplase, and tenecteplase; anistreplase; streptokinase; and urokinase, among others. Optionally or additionally, anticoagulant drugs such as heparin may be administered to minimize further generation of thrombi or emboli.

While the present invention has been described in terms of preferred embodiments, it will be understood, of course, that the invention is not limited thereto since modifications may be made to those skilled in the art, particularly in light of the foregoing teachings.

The invention claimed is:

1. An intravascular device for capturing emboli, the intravascular device comprising:
    a device body having a longitudinal axis and comprising:
        a filter basket comprising a filter portion and a lip attached to the filter portion, the lip defining an opening to the filter portion, the filter portion extending distally to a filter end from the lip and having apertures formed therethrough for blood flow; and
        a plurality of elongate members each having a proximal end and a distal end, the distal ends being attached to and disposed circumferentially on the lip of the filter basket, each elongate member extending proximally to its proximal end, the elongate members defining a device interior therebetween; and
        a flexible arm comprising a nonmagnetic material, the flexible arm having a first end attached to the device body and extending into the device interior to a second end, a magnetic element being disposed at the second end of the flexible arm such that movement of the flexible arm is indicative of capture of emboli within the filter portion.

2. The intravascular device according to claim 1 wherein the first end of the flexible arm is attached to the lip of the basket.

3. The intravascular device according to claim 1 wherein the first end of the flexible arm is attached to an elongate member.

4. The intravascular device according to claim 1 wherein the flexible arm is formed integrally with the device body.

5. The intravascular device according to claim 1 wherein the proximal ends of the elongate members are attached at a proximal hub.

6. The intravascular device according to claim 1 wherein the second end of the flexible arm is free to move during systole and diastole.

7. The intravascular device according to claim 1 wherein the basket comprises a nickel-titanium alloy.

8. The intravascular device according to claim 1 further comprising a sleeve attached to the lip of the basket portion and extending proximally to a proximal portion, the sleeve surrounding the elongate members, at least one hole being formed through the sleeve at its proximal portion.

9. The intravascular device according to claim 1 wherein the basket comprises woven polymer fibers.

10. The intravascular device according to claim 1 wherein the flexible arm comprises a nickel-titanium alloy.

11. The intravascular device according to claim 1 wherein the device body comprises a material which releases nitric oxide into the bloodstream of a patient in which it is installed.

12. The intravascular device according to claim 1 wherein the flexible arm and the elongate members are coated with a coagulation-inhibiting material.

13. The intravascular device according to claim 1 wherein the basket has a substantially semispherical shape.

14. A system for detecting embolic fragments in an intravascular device, the system comprising:
    an intravascular device for capturing emboli comprising:
        a device body having a longitudinal axis and comprising:
            a filter basket comprising a filter portion and a lip attached to the filter portion, the lip defining an opening to the filter portion, the filter portion extending distally to a filter end from the lip and having apertures formed therethrough for blood flow; and
            a plurality of elongate members each having a proximal end and a distal end, the distal ends being attached to and disposed circumferentially on the lip of the filter basket, each elongate member extending proximally to its proximal end, the elongate members defining a device interior therebetween; and
            a flexible arm comprising a nonmagnetic material, the flexible arm having a first end attached to the device body and extending into the device interior to a second end, a magnetic element being disposed at the second end of the flexible arm such that movement of the flexible arm generates a signal indicative of capture of emboli within the filter portion; and
        a detector for detecting the signal generated by the flexible arm, the signal comprising at least one of a voltage, a current, and an electromagnetic field.

15. The system according to claim 14, wherein the first end of the flexible arm is attached to the lip of the basket.

16. The system according to claim 14, wherein the first end of the flexible arm is attached to an elongate member.

17. The system according to claim 14, wherein the flexible arm is formed integrally with the device body.

18. A method for detecting embolic fragments in a blood vessel, the method comprising:
    implanting an intravascular device having a device body into the blood vessel, the device comprising a filter basket, the device having a flexible arm therewithin comprising a magnetic element, the flexible arm having a first end attached to the device body and extending to a second end, the flexible arm comprising a nonmagnetic material and having a magnet disposed at the second end, such that movement of the flexible arm is indicative of blood flow through the filter basket defining a baseline signal;
    generating an experimental signal; and
    comparing the experimental signal to the baseline signal to determine the presence of captured emboli within the intravascular device.

19. The method of claim 18, wherein the baseline signal and the current signal comprise a measurement of current.

20. The method of claim 18, wherein the baseline signal and the current signal comprise a measurement of voltage.

\* \* \* \* \*